(12) United States Patent
Bougaret et al.

(10) Patent No.: US 8,124,640 B2
(45) Date of Patent: Feb. 28, 2012

(54) PHARMACEUTICAL COMPOSITION BASED ON IDAZOXAN, SALTS, HYDRATES OR POLYMORPHS THEREOF

(75) Inventors: Joël Bougaret, Francarville (FR); Jean-Louis Avan, Villefrance de Lauragais (FR); Roland Segonds, Toulouse (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 815 days.

(21) Appl. No.: 12/015,788

(22) Filed: Jan. 17, 2008

(65) Prior Publication Data
US 2008/0113022 A1    May 15, 2008

Related U.S. Application Data

(62) Division of application No. 10/722,451, filed on Nov. 28, 2003, now Pat. No. 7,338,970.

(30) Foreign Application Priority Data

Oct. 28, 2003    (FR) ..................... 03 12626

(51) Int. Cl.
*A61K 31/415* (2006.01)
*A61K 31/35* (2006.01)
(52) U.S. Cl. ........................ 514/402; 514/454
(58) Field of Classification Search .................. 514/402, 514/454
See application file for complete search history.

(56) References Cited

U.S. PATENT DOCUMENTS

| 4,818,764 A | 4/1989 | Chapleo et al. |
| 5,487,901 A | 1/1996 | Conte et al. |
| 5,492,907 A | 2/1996 | Pickar et al. |

FOREIGN PATENT DOCUMENTS

| FR | 92-14694 A1 | 12/1992 |
| FR | 96-03674 A1 | 3/1996 |
| WO | WO-01/39740 A1 | 6/2001 |

OTHER PUBLICATIONS

Haleblian et al. Pharmaceutical Applications of Polymorphism. Journal of Pharmaceutical Sciences, vol. 58, No. 8, 1969, pp. 911-929.*
Rouhi et al. The Right Stuff. Chemical and Engineering News. vol. 81, No. 8, pp. 32-35, 2003.*
Reckitt & Colman, "Idazoxan Hydrochloride", Drug of the Future, 10, p. 782, 1985.
F.C. Colpaert, "Pharmacological Characteristics of Tremor,, Rigidity and Hypokinesia Induced by Reserpine in Rat", Neuropharmacology, vol. 26, No. 9, pp. 1431-1440, 1987.
F.C. Colpaert, "Effect of an Alpha Antagonist in a 20-Year Old Java Monkey With MPTP-Induced Parkinsonian Signs", Brain Research Bulletin, vol. 26, pp. 627-631, 1991.
B. Scatton et al., Behavioural Pharmacology 2000, vol. 11, Nos. 3 and 4, 243-256.

* cited by examiner

*Primary Examiner* — Sreeni Padmanabhan
*Assistant Examiner* — Renee Claytor
(74) *Attorney, Agent, or Firm* — Birch, Stewart, Kolasch & Birch, LLP

(57) ABSTRACT

Pharmaceutical composition comprising 5 to 20% of an idazoxan salt or of idazoxan hydrate, 10 to 40% of microcrystalline cellulose, 1 to 5% of lubricant, 0.1 to 0.5% of colloidal silica and from 29.5% to 84.8% of lactose, with respect to the total mass.

1 Claim, 7 Drawing Sheets

Figure 1:
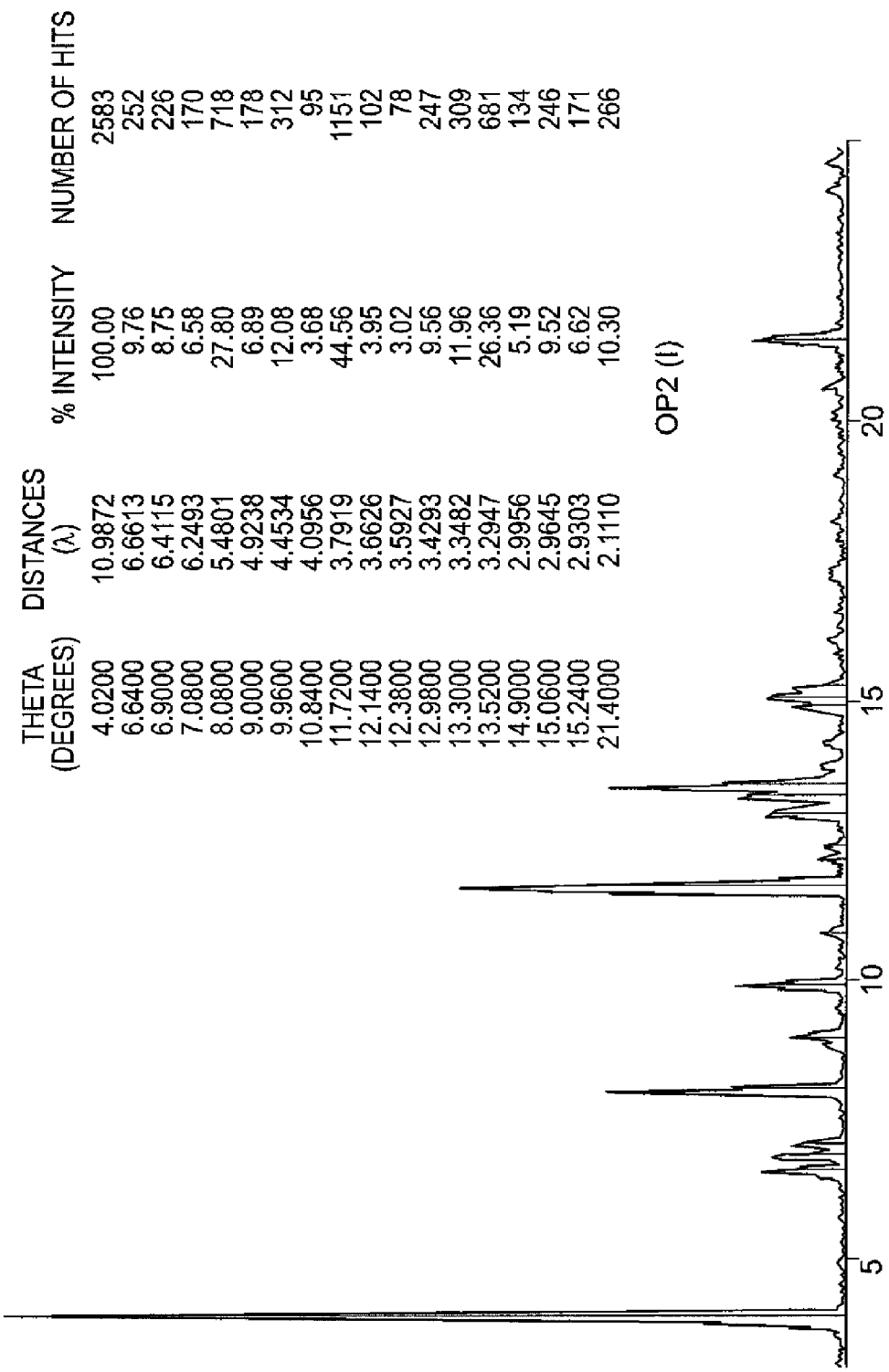

PHARMACEUTICAL COMPOSITION BASED ON IDAZOXAN, SALTS, HYDRATES OR POLYMORPHS THEREOF

CROSS-REFERENCE TO RELATED APPLICATIONS

The present application is a 37 C.F.R. §1.53 divisional of U.S. application Ser. No. 10/722,451 filed Nov. 28, 2003 now U.S. Pat. No. 7,338,970, which claims priority on French Patent Application No. 0312626 filed Oct. 28, 2003. Each application is hereby incorporated by reference.

The present invention relates to the pharmaceutical industry and concerns the pharmaceutical dosage formulation of active principle. More particularly, the invention relates to a stable formulation, suited to industrial production, of non-film-coated tablets of idazoxan salt comprising a dose of active principle of between 5 and 100 mg and having a conventional release. These tablets are provided in a packaging which is leaktight to water vapour. Preferably, the idazoxan salt used is an idazoxan hydrochloride polymorph.

Idazoxan is known for its antagonist properties with regard to $\alpha_2$-adrenergic receptors. This compound is disclosed in Patent EP 033 655 by its chemical structure, its process of synthesis, certain pharmaceutical formulations and its therapeutic application as antidepressant medicament. Idazoxan has been studied in human clinical medicine in the treatment of depression at doses varying between 5 and 40 mg, three times a day, over four weeks and showed a significant improvement on the Hamilton scale against placebo (Drug of the Future, 10, No. 9, 782, 1985). Various studies have also been carried out on monkeys or rats to evaluate the effects of the various compounds on symptoms analogous to those of Parkinson's disease, such as the symptoms induced by reserpine in the rat (F. C. Colpaert, Neuropharmacologie, 26, 1431, 1987) or by the neurotoxin MPTP (F. C. Colpaert et al., Brain. Res. Bul., 26, 627, 1991). More specifically, Patent FR 92/14694 relates to the use of idazoxan and of its derivatives in the preparation of a medicament intended for the treatment of Parkinson's disease, its progression in its idiopathic form and its evolution. Patent Application FR 96/03674 relates to products comprising milnacipran and idazoxan as combined pharmaceutical preparation for a simultaneous, separate or sequential use in treating depression and its various forms, and pathologies in which antidepressants are used.

Several problems have to be solved before envisaging the large-scale industrial use of idazoxan. In particular, it is necessary to find an excipient compatible with this active principle, to select a form of vehicle suitable for guaranteeing its stability and to look for a manufacturing process, taking into account in particular the problem of hygroscopicity of idazoxan and its stability. Furthermore, the active principle has to exhibit suitable physical properties in terms of particle size and of tabletability. It is therefore necessary to choose a suitable leaktight packaging which protects the active principle from moisture. These are the problems, still unsolved, which the present invention intends to solve.

The present invention relates to a pharmaceutical composition comprising 5 to 25% of a salt or of hydrate of idazoxan or of its derivatives, 10 to 40% of micro-crystalline cellulose, 0.1 to 5% of lubricant, and from 0.1 to 0.5% of colloidal silica and from 25 to 90% of lactose, with respect to the total mass. Preferably, the present invention relates to a pharmaceutical composition comprising 5 to 20% of an idazoxan salt or of idazoxan hydrate, 10 to 40% of microcrystalline cellulose, 1 to 5% of lubricant, 0.1 to 0.5% of colloidal silica and from 29.5% to 84.8% of lactose, with respect to the total mass.

The term "idazoxan and its derivatives" is understood to mean the compound of general formula I:

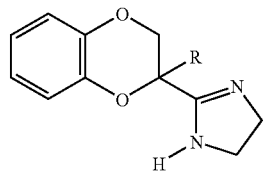

in which R represents a hydrogen atom, a linear or branched $C_1$-$C_4$ alkyl radical and a linear or branched $C_1$-$C_4$ alkoxy radical, and its therapeutically acceptable salts, its racemate or its optically active isomers. Preferably, R represents a hydrogen atom, a methoxy radical or an n-propyl radical. One aspect of the present invention thus relates to a stable formulation, as defined above, comprising idazoxan of formula II:

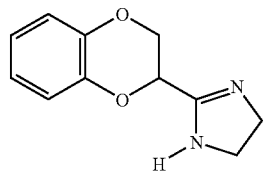

Idazoxan hydrochloride has a proton at the $C_2$ chiral centre, with the result that two potential R(−) and S(+) enantiomers exist. The pharmaceutical composition according to the invention preferably comprises the racemic mixture but it is possible to envisage the idazoxan of the composition being enriched in one or other of the enantiomers, indeed even comprising virtually exclusively one or other of the enantiomers, given that it is possible to separate the two stereoisomers by means, for example, of a chiral column. The two enantiomers have different pharmacokinetic characteristics (see Example 8) but, even if the two enantiomers are separated, there exists an inter-conversion from one form to the other both in vitro (under physiological conditions, pH 7.4, 37° C.; see Example 8.1) and in vivo (see Example 8.2).

In a preferred embodiment, the idazoxan salt is idazoxan hydrochloride and the lubricant is glyceryl behenate, magnesium stearate being incompatible with the active principle.

The pharmaceutical composition according to the invention is particularly suited to industrial production and is stable. A formulation is described as "able to be produced industrially" or "suited to industrial production" when the formulation makes it possible to obtain batches on a rotary production device while satisfying the main tests of the European Pharmacopoeia as regards tablets. The term "stable" is understood to mean packaged tablets which generate less than 1.5% of decomposition impurity after one month at 40° C., 75% RH (Relative Humidity), and at most 2% of impurity after 2 years at 25° C., 60% RH.

In an even more preferred embodiment, the idazoxan salt is chosen from the polymorphs of form I, II, III, IV and V or a mixture of at least two, of at least three, of at least 4 or 5 idazoxan polymorphs. The pharmaceutical composition is not intended to be limited to the polymorphs of idazoxan or to a mixture of polymorphs of idazoxan. Other idazoxan-based compounds suited to use in this pharmaceutical composition are presented in U.S. Pat. Nos. 2,979,511 and 4,818,764.

Figure 4:
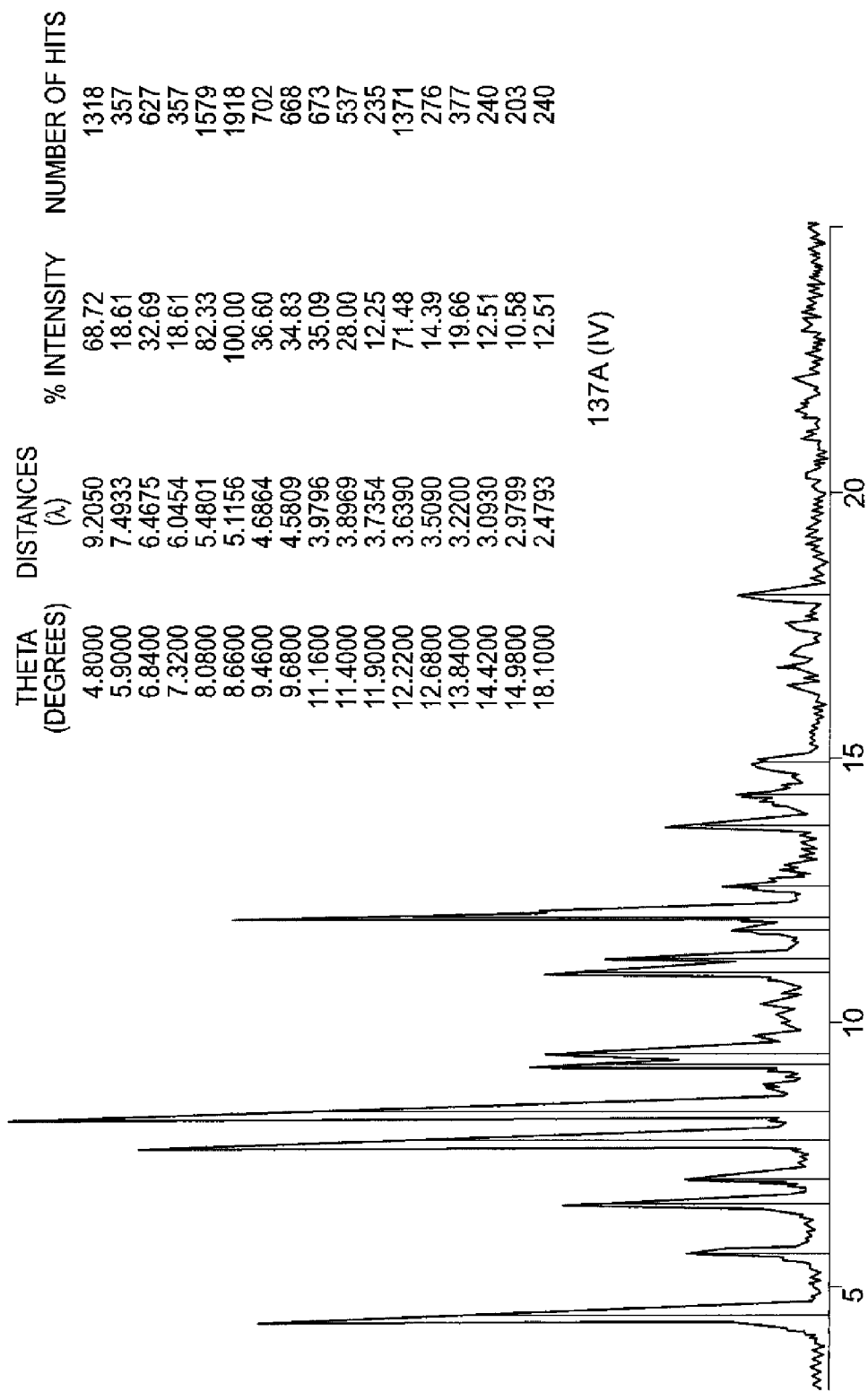
Figure 5:
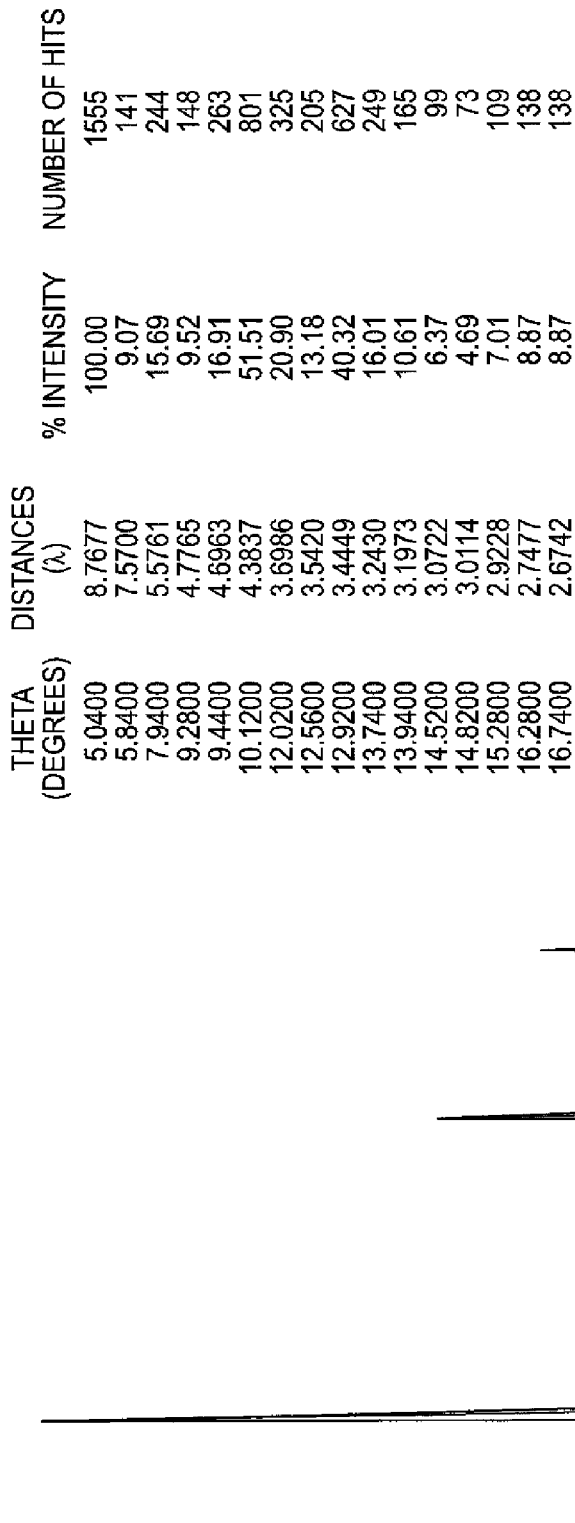
Figure 6:
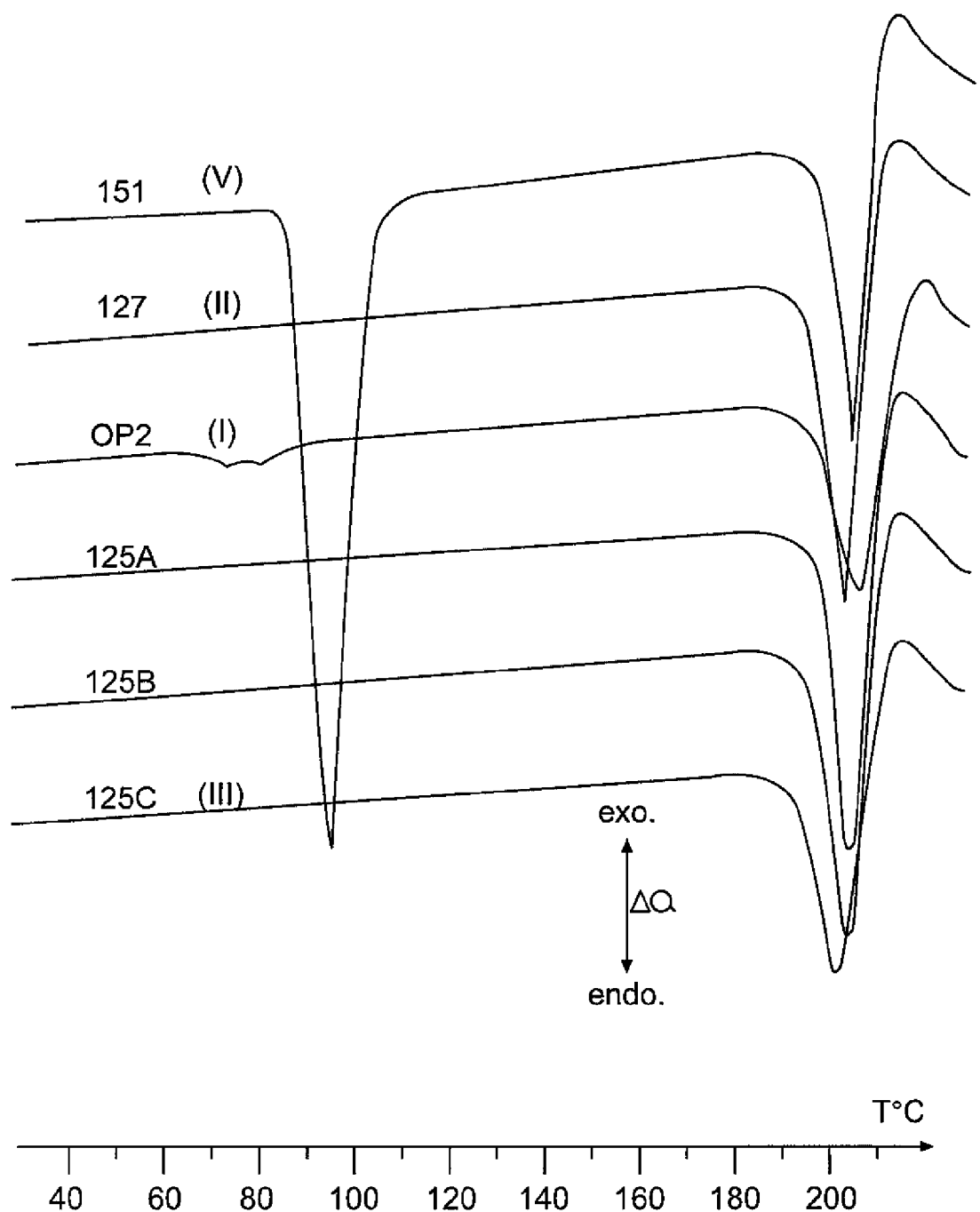
Figure 7:
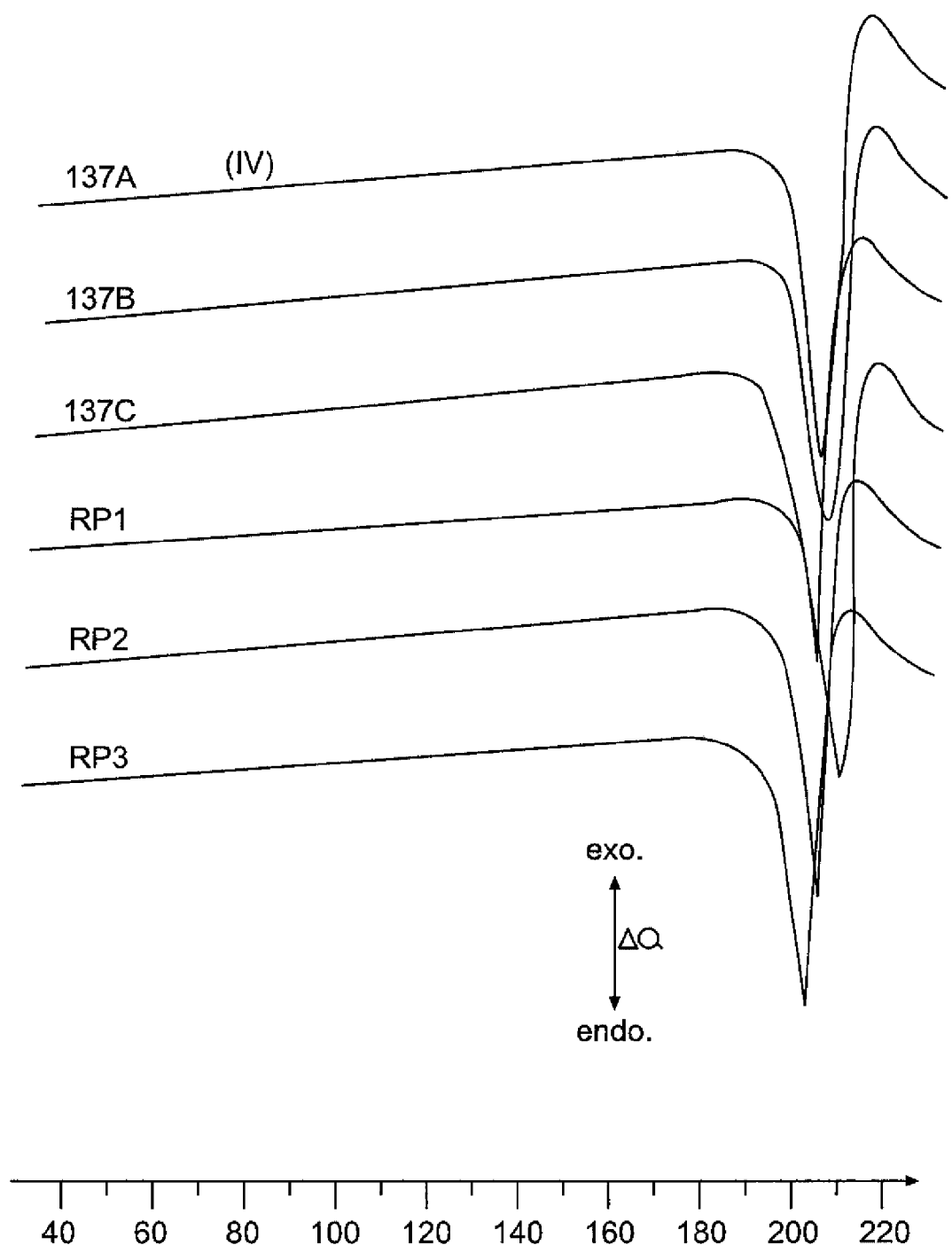

The polymorphs are characterized by the X-ray diffraction spectra presented respectively in FIGS. 1, 2, 3, 4 and 5 and are also characterized by the differential thermal analysis thermograms presented in FIGS. 6 and 7, measured using a Mettler FP 800. The X-ray diffraction spectrum and the differential thermal analysis thermogram, measured using a Mettler FP 800, of idazoxan hydrochloride (form II) are presented in FIGS. 2 and 6 respectively. As regards the differential thermal analysis, it should be pointed out that the use of another make or of another model of differential thermal analysis device (for example, Perkin-Elmer) can result in a different thermogram. The present invention is characterized by the values of the thermogram which are presented here and which are obtained using a Mettler FP 800 and by the values of an equivalent thermogram which are obtained using other types of differential thermal analysis devices.

It is also one of the objects of the present invention to protect these five forms I, II, III, IV and V as such.

The polymorph of form I is characterized by an X-ray diffraction spectrum comprising characteristic peaks at approximately 4.0200, 6.6400, 6.9000, 7.0800, 8.0800, 9.0000, 9.9600, 9.9600, 10.8400, 11.7200, 12.1400, 12.3800, 12.9800, 13.3000, 13.5200, 14.9000, 15.0600, 15.2400 and 21.4000 degrees θ. The polymorph of form I is also characterized by an X-ray diffraction spectrum comprising characteristic peaks at approximately 4.0200, 6.6400, 6.9000, 7.0800, 8.0800, 9.0000, 9.9600, 9.9600, 10.8400, 11.7200, 12.1400, 12.3800, 12.9800, 13.3000, 13.5200, 14.9000, 15.0600, 15.2400 and 21.4000 degrees θ and lacking at least one peak at approximately 4.7400, 5.7200, 8.9200, 16.8600 or 18.9000 degrees θ. The polymorph of form I is also characterized by a differential thermal analysis thermogram exhibiting a single maximum value at approximately 207.5±0.2.

The polymorph of form II is characterized by an X-ray diffraction spectrum comprising characteristic peaks at approximately 4.7400, 5.7200, 6.6800, 7.5000, 8.9200, 9.9600, 11.5200, 12.3000, 12.9400, 13.5400, 14.3000, 15.6800, 16.8600 and 18.9000 degrees θ. The polymorph of form II is also characterized by a differential thermal analysis thermogram exhibiting a single maximum value at approximately 203.9±0.4.

The polymorph of form III is characterized by an X-ray diffraction spectrum comprising characteristic peaks at approximately 4.0400, 4.7000, 5.7400, 6.6200, 6.9200, 7.4600, 8.0400, 8.7800, 8.9800, 9.9800, 10.8200, 11.4600, 11.6400, 12.3200, 12.9400, 13.5400, 14.2400, 15.0600, 15.6200 and 16.8400 and degrees θ. The polymorph of form III is also characterized by a differential thermal analysis thermogram exhibiting a single maximum value at approximately 203.8±0.5.

The polymorph of form IV is characterized by an X-ray diffraction spectrum comprising characteristic peaks of approximately 4.8000, 5.9000, 6.8400, 7.3200, 8.0800, 8.6600, 9.4600, 9.6800, 11.1600, 11.4000, 11.9000, 12.2200, 12.6800, 13.8400, 14.4200, 14.9800 and 18.1000 degrees θ. The polymorph of form IV is also characterized by an X-ray diffraction spectrum comprising characteristic peaks at approximately 4.8000, 5.9000, 6.8400, 7.3200, 8.0800, 8.6600, 9.4600, 9.6800, 11.1600, 11.4000, 11.9000, 12.2200, 12.6800, 13.8400, 14.4200, 14.9800 and 18.1000 degrees θ and lacking at least one peak at approximately 6.6800, 13.5400, 15.6800, 16.8600 or 18.9000 degrees θ. The polymorph of form IV is also characterized by a differential thermal analysis thermogram exhibiting a single maximum value at approximately 205.3±0.5.

The polymorph of form V is an idazoxan hydrochloride monohydrate which is characterized by an X-ray diffraction spectrum comprising characteristic peaks at approximately 5.0400, 5.8400, 7.9400, 9.2800, 9.4400, 10.1200, 12.0200, 12.5600, 12.9200, 13.7400, 13.9400, 14.5200, 14.8200, 15.2800, 16.2800 and 16.7400 degrees θ. The polymorph of form V is also characterized by an X-ray diffraction spectrum comprising characteristic peaks at approximately 5.0400, 5.8400, 7.9400, 9.2800, 9.4400, 10.1200, 12.0200, 12.5600, 12.9200, 13.7400, 13.9400, 14.5200, 14.8200, 15.2800, 16.2800 and 16.7400 degrees θ and lacking at least one peak at approximately 4.7400, 6.6800, 7.5000, 8.9200, 11.5200, 14.3000, 15.6800 or 18.9000 degrees θ. The idazoxan monohydrate polymorph of form V is also characterized by a differential thermal analysis thermogram exhibiting a single maximum value at approximately 205.6±0.4.

The invention provides a method for the synthesis of the idazoxan polymorph of form I according to a process comprising the following stages: (i) reaction of catechol and 2-chloroacrylonitrile in the presence of pulverized potassium carbonate and of a catalyst, such as tetrabutylammonium bromide, in a mixture of toluene and of dioxane, (ii) evaporation of the toluene and production of a racemic mixture of 2-cyano-1,4-benzodioxane, (iii) cyclization of the 2-cyano-1,4-benzodioxane in the presence of ethylenediamine and of hydrochloric acid, (iv) addition of hydrochloric acid to crystallize and to remove the excess ethylenediamine and (v) recrystallization of the idazoxan hydrochloride from ethanol. Thus it is that the polymorph of form I is obtained.

The present invention also provides a method for the synthesis of the idazoxan polymorphs of forms III and IV according to a process comprising the following stages: (i) reaction of catechol and 2-chloroacrylonitrile in the presence of pulverized potassium carbonate and of a catalyst, such as tetrabutylammonium bromide, in a mixture of toluene and of dioxane, (ii) evaporation of the toluene and production of a racemic mixture of 2-cyano-1,4-benzo-dioxane, (iii) cyclization of the 2-cyano-1,4-benzodioxane in the presence of ethylenediamine and of hydrochloric acid, (iv) addition of hydrochloric acid to crystallize and to remove the excess ethylenediamine, (v) recrystallization of the idazoxan hydrochloride from ethanol and (vi) purification of the idazoxan hydrochloride by recrystallization either with ethanol, to obtain the form III, or with 1-butanol, to obtain the form IV. Thus it is that the polymorphs III and IV are obtained.

The present invention also provides a method for the synthesis of an idazoxan hydrochloride monohydrate, denoted in the present document as form V, according to a process comprising the following stages: (i) reaction of catechol and 2-chloroacrylonitrile in the presence of pulverized potassium carbonate and of a catalyst, such as tetrabutylammonium bromide, in a mixture of toluene and of dioxane, (ii) evaporation of the toluene and production of a racemic mixture of 2-cyano-1,4-benzodioxane, (iii) cyclization of the 2-cyano-1,4-benzodioxane in the presence of ethylenediamine and of hydrochloric acid, (iv) addition of hydrochloric acid to crystallize and to remove the excess ethylenediamine, (v) recrystallization of the idazoxan hydrochloride from ethanol and (vi) reslurrying in five volumes of a mixture of 80% of acetone and of 20% of water. Thus it is that the monohydrate is obtained. The invention also encompasses the hydrates of idazoxan and the pharmaceutical compositions comprising such hydrates. The term "hydrate" covers, but without implied limitation, hemihydrates, monohydrates, dihydrates, trihydrates and other substances of the same type.

The composition according to the invention is administered orally and is thus formulated in a form suitable for oral administration, preferably in the solid form. Mention may be made, among suitable solid oral presentations, of: tablets, hard gelatin capsules, granules and other presentations of the same type. The pharmaceutical compositions suitable for oral administration comprise, in addition to the polymorphic compounds of the present invention, or their mixtures, their derivatives, their analogues or their pharmaceutically acceptable salts or hydrates, a carrier, a diluent or an excipient which is also acceptable pharmaceutically. Any inert excipient, commonly used as carrier or diluent, can be used in the compositions of the present invention, whether they are, for example, gums, starches (for example, maize starch, pregelatinized starch), sugars (for example lactose, mannitol, sucrose or dextrose), cellulose materials (for example, microcrystalline cellulose), acrylates (for example, poly(methyl acrylate)), calcium carbonate, magnesium oxide, talc, or mixtures of these. A preferred diluent is lactose monohydrate. When they are provided in the form of solid tablets, the compositions can additionally comprise a disintegrating agent (for example, microcrystalline cellulose), a lubricant (for example, glyceryl behenate) and a flow agent (for example, colloidal silica).

In a preferred embodiment, the pharmaceutical composition comprises idazoxan hydrochloride, lactose monohydrate, microcrystalline cellulose, glyceryl behenate and colloidal silica. More preferably, the pharmaceutical composition comprises 10% by weight of idazoxan hydrochloride, 61.46% by weight of lactose monohydrate, 26.34% by weight of microcrystalline cellulose, 2% by weight of glyceryl behenate and 0.2% by weight of colloidal silica.

In one embodiment of the present invention, the composition is formulated in the form of tablets which preferably have a mass of between 50 mg and 1 000 mg, preferably between 100 and 600 mg, more preferably approximately 100 mg, 200 mg, 300 mg, 400 mg or approximately 500 mg.

The present invention also encompasses pharmaceutical compositions comprising any solid or liquid physical form of any one of the idazoxan polymorphs described here. For example, the idazoxan polymorphs can be provided in a crystalline form and can have any particle size. The particles of the idazoxan polymorphs can be micronized or agglomerated and can be provided in the form of particulate granules, of powders or of any other solid physical form, the preferred embodiment corresponding to a solid form.

It is particularly advantageous to formulate the oral compositions in the unit dosage form for easier administration and a uniform dosage. The unit dosage form as used here refers to physically discrete units suitable for a unit dosage for the subject to be treated; each unit comprising a predetermined amount of active compound calculated to produce the desired therapeutic effect in combination with the required pharmaceutical vector. The specifications of the unit dosage forms of the invention are dictated by the unique characteristics of the active compound and by the specific therapeutic effect which has to be obtained, and by the limitations inherent in the art of the composition of such an active compound for the treatment of individuals, these specifications also depending directly on the above elements.

The pharmaceutical compositions can be present in a packaging, a container or a distributing device at the same time as the instructions for use.

Advantageously, the said tablets are provided in a leaktight packaging which can be composed of a tablet bottle made of polypropylene or of high-density polyethylene, an aluminium sachet or an "all-aluminium" blister pack.

An additional aspect of the present invention is targeted at a process for the manufacture of the said compositions by direct tabletting of a powder mixture. This manufacturing process is preferred to a process involving a stage of granulation with a wetting liquid as, surprisingly, a conventional binder, such as povidone, is incompatible with this active principle. Alternatively, the direct tabletting process comprises a stage of dry granulation, for example by compacting, which precedes the tabletting stage. In the process for manufacturing by tabletting, the idazoxan salt has a particle size, expressed by its mean diameter, of between 50 and 250 microns, preferably of between 75 and 150 microns and more particularly in the region of 100 to 125 microns. Furthermore, the idazoxan salt or the idazoxan hydrate has a bulk density of between 0.4 and 0.8 and preferably of between 0.5 and 0.7 and more preferably still in the region of 0.6.

The present invention is also targeted at the use of the said compositions in the manufacture of a medicament, in particular in the manufacture of a medicament intended for the preventive and/or curative treatment of disorders of the central nervous system. Preferably, the medicament in the form of a tablet is intended for the treatment of depression, Parkinson's disease and/or severe psychotic disorders, such as schizophrenia and schizoaffective disorders.

According to another preferred embodiment, the medicament is used in combination with a second medicament, preferably an atypical neuroleptic, more preferably an atypical neuroleptic exhibiting a greater antagonist affinity for the dopamine $D_2$ receptor than is its antagonist affinity for the $\alpha_2$-adrenoreceptor, for the preventive and/or curative treatment of serious psychotic mental disorders, in particular schizophrenia and schizoaffective disorders. For a definition of atypical neuroleptics, see U.S. Patent Applications US 60/398,718 and US 60/398,719, filed on 29 Jun. 2002. Mention may be made, among atypical neuroleptics, of olanzapine, quetiapine, risperidone, sertindole or ziprasidone. More preferably, the atypical neuroleptic is olanzapine. The administration of the said first medicament and of the said second medicament is carried out simultaneously, separately or sequentially, in any order.

Other characteristics and advantages of the invention will become apparent in the continuation of the description with the examples represented below. In these examples, reference will be made to the following figures. These figures and examples are intended to illustrate the present invention and may not under any circumstances be interpreted as being able to limit the scope thereof.

KEYS TO THE FIGURES

Figure 2:
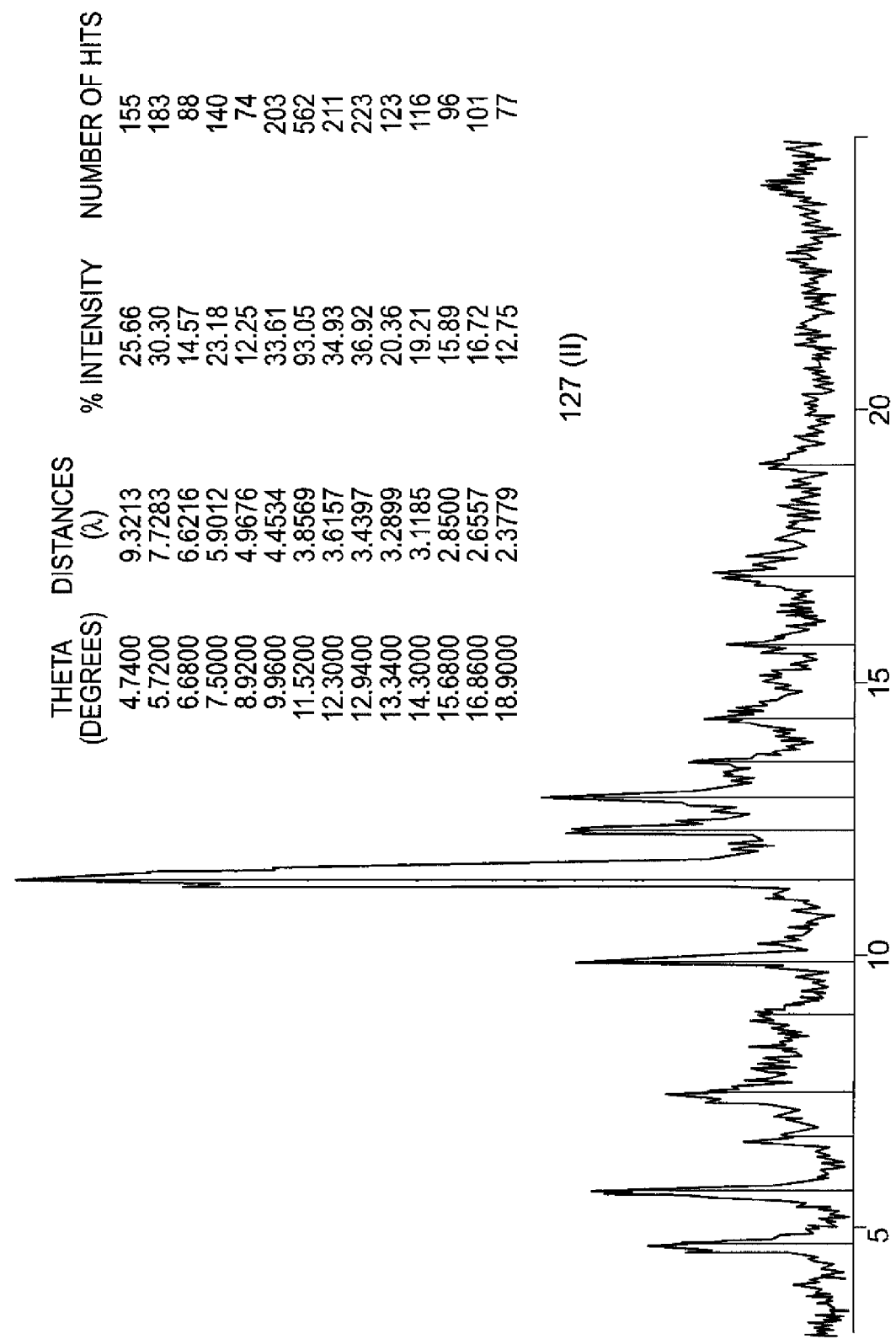
Figure 3:
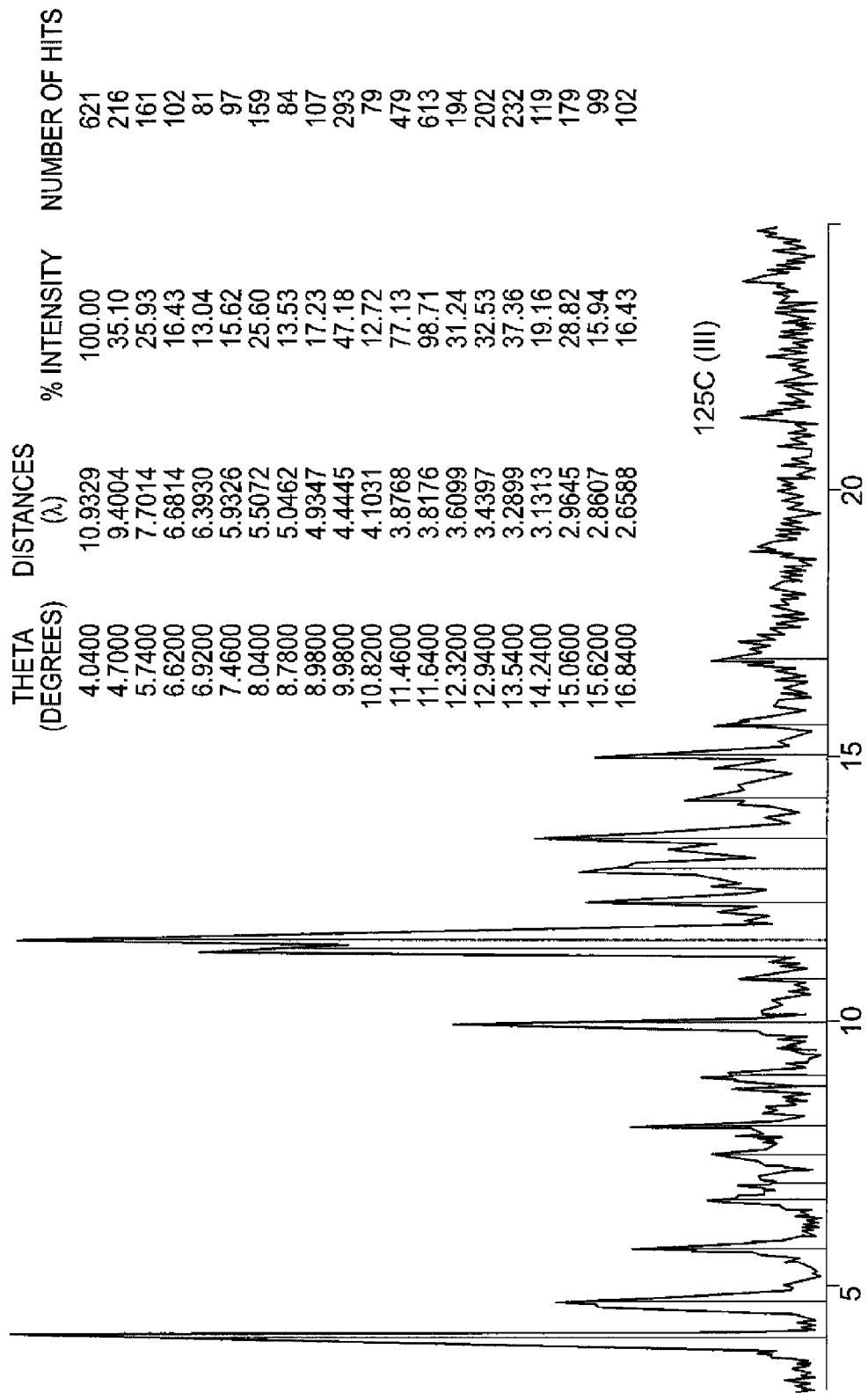

FIG. 1: X-ray diffraction diagram for the idazoxan hydrochloride polymorph of form I;

FIG. 2: X-ray diffraction diagram for the idazoxan hydrochloride polymorph of form II;

FIG. 3: X-ray diffraction diagram for the idazoxan hydrochloride polymorph of form III;

FIG. 4: X-ray diffraction diagram for the idazoxan hydrochloride polymorph of form IV;

FIG. 5: X-ray diffraction diagram for idazoxan hydrochloride monohydrate of form V;

FIG. 6: Differential thermal analysis thermogram for the idazoxan hydrochloride polymorph of form I, II, III and V;

FIG. 7: Differential thermal analysis thermogram for the idazoxan hydrochloride polymorph of form IV.

EXAMPLES

Example No. 1

Stability Study on Formulations Comprising Idazoxan Hydrochloride

Idazoxan hydrochloride belongs to the category of $\alpha_2$-adrenoreceptor antagonists. The chemical name of this molecule is 2-(2-imidazolinyl)-1,4-benzodioxane hydrochloride and its molecular formula is $C_{11}H_{12}N_2O_2 \cdot HCl$.

Idazoxan is provided in the form of a slightly hygroscopic, white to substantially white powder which is readily soluble in water and methanol and which is soluble to fairly soluble in ethanol.

Because of its slight hygroscopicity, it has to be stored in a leaktight packaging, with exclusion of moisture.

During all the tests carried out, this molecule exhibited the following characteristics:
- Idazoxan hydrochloride content of between 99.0 and 101.0%
- Individual content of known impurities $\leqq 0.2\%$
- Individual content of unknown impurities $\leqq 0.1\%$
- Total content of impurities $\leqq 1.0\%$ The main impurity of idazoxan hydrochloride is known as 791011: N-(2-aminoethyl)-1,4-benzodioxane-2-carboxamide.

The stability of the active principle was studied under various conditions of stress:
- +4° C. in a closed bottle (reference)
- 50° C., open bottle
- 40° C., 30% RH, open bottle
- 40° C., 75% RH, open bottle Whatever the conditions, idazoxan hydrochloride does not undergo any organoleptic change and no significant chemical instability is observed, even for high relative humidities (percentage of 791011 $\leqq 0.03\%$ and absence of unknown impurities).

Compatibility studies were carried out at 40° C., 75% RH, for 1 month between idazoxan hydrochloride and various conventional excipients of the dry forms.

The results obtained are displayed in Table 1 below and express the surprising difference in behaviour of the binary mixtures between monitoring immediately after manufacturing and monitoring after 1 month under stressing conditions, whereas the active principle alone is perfectly stable.

TABLE 1

| Excipient | Active principle/Excipient Ratio | % 791011 | Function |
|---|---|---|---|
| Lactose monohydrate | 1/4 | 0.1 | Diluents |
| Anhydrous lactose | 1/4 | 0.3 | |
| Mannitol | 1/4 | 0.3 | |
| Sorbitol | 1/4 | 40.8 | |
| Microcrystalline cellulose | 1/2 | 3.7 | Diluent/Binder/Disintegrating agent |
| Calcium carboxymethylcellulose | 1/2 | 4.4 | Disintegrating agent |
| Povidone | 4/1 | 8.5 | Binder |
| Hydroxypropylmethylcellulose (HPMC) | 4/1 | 1.5 | Binder |
| Magnesium stearate | 4/1 | 17.0 | Lubricant |
| Talc | 4/1 | 1.0 | Glidant |

The excipients which are most compatible with idazoxan hydrochloride are lactose, mannitol, microcrystalline cellulose and HPMC. This study shows the high reactivity of idazoxan hydrochloride in the presence of excipients conventionally used in pharmaceutical formulating.

A conventional gelatin-based hard gelatin capsule form was developed in preparing the first formulations of this molecule.

Lactose or mannitol were used as diluents because of the results of the binary compatibilities. These diluents were used in combination with conventional lubrication excipients: talc and magnesium stearate.

These formulations were lubricated with talc and magnesium stearate despite the negative result obtained with magnesium stearate, this being done in order to confirm this incompatibility at the real level of use of magnesium stearate.

The hard gelatin capsules manufactured were packaged in a leaktight packaging (polypropylene tablet bottle) because of the slight hygroscopicity of the active principle and because of the risk of ring opening with the formation of the impurity 791011 (product itself reactive).

The compositions of the formulations prepared are presented in Table 2 below:

TABLE 2

| Component | Formulation 1 | Formulation 2 | Formulation 3 | Function |
|---|---|---|---|---|
| Idazoxan hydrochloride | 20 mg | 20 mg | 20 mg | Active principle |
| Anhydrous lactose | 130.2 mg | 0 | 0 | Diluents |
| Lactose monohydrate | 0 | 0 | 158 mg | |
| Mannitol | 0 | 130.2 mg | | |
| Microcrystalline cellulose | 0 | 0 | 20 mg | |
| Magnesium stearate | 0.8 mg | 0.8 mg | 2 mg | Lubricant |
| Talc | 4.0 mg | 4.0 mg | 0 | |
| Hard gelatin capsules, size 3 | | | | |

After 1 month under stable conditions in a tablet bottle at 40° C., 75% RH, the analyses show a totally unacceptable level of decomposition product (cf. Table 3 below):

TABLE 3

| | Formulation 1 | Formulation 2 | Formulation 3 |
|---|---|---|---|
| Percentage of 791011 | 3.0% | 2.0% | 2.9% |

It is therefore impossible to formulate idazoxan hydrochloride in a simple hard gelatin capsule formulation; a posteriori, it has been demonstrated that this active principle is incompatible with gelatin.

Furthermore, the formulations demonstrate the incompatibility of magnesium stearate.

The tablet formulation proves to be necessary in order to provide satisfactory stability of the active principle. Furthermore, an alternative to magnesium stearate has been identified with glyceryl behenate.

In order to provide good homogeneity of distribution of the active principle, as far as possible independently of the physical characteristics of the active principle, and of the excipients, tablet manufacture by wet granulation is studied first.

Wet granulation was carried out in a high-speed mixer/granulator with water. The granules obtained are dried in a fluidized air bed and then graded on a 0.4 mm screen.

Two procedures were selected:
  Either granulation of all the diluent, binder/disintegrating agent and active principle. After granulation, drying and sieving, lubrication is carried out by mixing the particle with the lubricant.
  Or granulation of half the diluent and half the binder/disintegrating agent with all the active principle. After granulation, drying and sieving, mixing the particle with the other half of the binder/disintegrating agent and diluent, then addition of the lubricant last and mixing.

The tablets were subsequently packaged in all-aluminium blister packs or in leaktight tablet bottles.

The formulations employed and the pharmacotechnical results are described respectively in Tables 4 and 5 below:

TABLE 4

| Starting material | Formulation 4 | Formulation 5 | Formulation 6 | Formulation 7 |
|---|---|---|---|---|
| Idazoxan hydrochloride | 20 mg (5%) | 20 mg (10%) | 30 mg (10%) | 30 mg (20%) |
| Diluent: lactose | 332 mg | 156 mg | 205 mg | 104 mg |
| Lubricant: glyceryl behenate | 8 mg | 4 mg | 5 mg | 4 mg |
| Binder/disintegrating agent: microcrystalline cellulose | 40 mg (10%) | 20 mg (10%) | 60 mg (20%) | 21 mg (15%) |
| | 0 0 | 0 0 | 0 0 | |
| TOTAL | 400 mg | 200 mg | 300 mg | 140 mg |

Granulation was carried out with 10% of wetting liquid with respect to the total mass of the tablet.

TABLE 5

| Starting material | Formulation 4 | Formulation 5 | Formulation 6 | Formulation 7 |
|---|---|---|---|---|
| % 791011 | 4.54% | 0.44% | 5.2% | <0.2% |
| Hardness | 30 N | 40 N | 40 N | Nonexistent |
| Splitting | — | — | — | +++ |

Additional studies carried out with a formulation qualitatively equivalent to the formulation 5 have shown that an idazoxan hydrochloride content of 10% with respect to the total mass of the tablet, in combination with a microcrystalline cellulose content of 10%, was that which made it possible to obtain the best compromise between the hardness of the tablets and the splitting during tableting.

The results obtained with regard to feasibility (hardness and splitting) are satisfactory in the range from 5 to 10% of idazoxan hydrochloride, in combination with 8% to 15% of binder/disintegrating agent of microcrystalline cellulose type.

Thus, experiments have been continued until the formulation No. 5 has been optimized; with this aim, two amounts of wetting liquid were tested: 5% and 20%.
  Formulation 8: 5% of wetting liquid
  Formulation 12: 20% of wetting liquid The results relating to these formulations are expressed in Table 6 below. The level of impurity was determined after one month at 40° C., 75% RH.

TABLE 6

| % of wetting liquid | Level of impurity 791011 | Hardness | Splitting | CV of content |
|---|---|---|---|---|
| 5% (formulation 5a) | 1.5% | 20 N | +++ | 8% |
| 20% (formulation 5b) | 2.3% | 20 N | — | 7 5 |

The degree of dilution studied for the active principle (10%) does not make it possible to achieve satisfactory homogeneities in mixing (coefficient of variation in content >6%), for from 5% to 20% of water used in wetting during the granulation.

Furthermore, the levels of decomposition obtained, although slightly lower, remain comparable with those obtained with the formulations tested in hard gelatin capsules (of between 1.5% and 2.3% of product 791011).

With regard to the manufacture of tablets, the alternative process to wet granulation is direct tableting. In view of the results obtained in granulation, it is therefore logical to study the possibilities of this process relating to idazoxan hydrochloride.

The pharmacotechnical characteristics of the active principle are as follows:
  Bulk density of between 0.5 g/ml and 0.8 g/ml
  Mean diameter of between 100 and 300 μm
  Favourable aptitude for tableting: on an alternating tablet press, if a force of 10 000 newtons is applied, the hardness of the tablets obtained with pure active principle (volume=1 cm$^3$) is between 10 N and 30 N with regard to a round format with an area of 1 cm$^2$.

The formulations employed are presented in Table 7 below:

TABLE 7

| Starting materials | Formulation 8 | Formulation 9 | Formulation 10 | Formulation 11 | Function |
|---|---|---|---|---|---|
| Idazoxan hydrochloride | 20 mg | 20 mg | 20 mg | 20 mg | Active principle |

TABLE 7-continued

| Starting materials | Formulation 8 | Formulation 9 | Formulation 10 | Formulation 11 | Function |
|---|---|---|---|---|---|
| Lactose monohydrate | 158 mg | 152 mg | 0 | 122.92 mg | Diluent |
| Mannitol | 0 | 0 | 158 mg | 0 | |
| Microcrystalline cellulose | 20 mg | 20 mg | 20 mg | 52.68 mg | Binder/disintegrating agent |
| Glyceryl behenate | 0 | 8 mg | 0 | 4 mg | Lubricant |
| Magnesium stearate | 2 mg | 0 | 2 mg | 0 | Lubricant |
| Anhydrous colloidal silica | 0 | 0 | 0 | 0.4 mg | Flow agent |
| TOTAL | | | 200 mg | | |

The tablets obtained were packaged in leaktight blister packs (all-aluminium).

The pharmacotechnical results obtained after manufacture are described in Table 8 below, along with the percentage of impurity found after 1 month at 40° C., 75% RH.

TABLE 8

| Results | Formulation 8 | Formulation 9 | Formulation 10 | Formulation 11 |
|---|---|---|---|---|
| Hardness (format D8R10) | 20 newtons | 21 newtons | 25 newtons | 50 newtons |
| Splitting | ++ | ++ | +++ | + |
| Sticking | + | ++ | +++ | + |
| CV in content | 5.1% | 8% | 7.4% | 4.1% |
| % Impurity 791011 | 1.78% | 2.41% | 1.12% | 1.03% |

The formulation 11 has the best hardness and exhibits the lowest level of impurity and therefore has been selected.

The formulations 8, 9 and 10 have hardnesses which are too low for it to be possible to envisage industrial manufacture on a rotary press. Furthermore, the splitting and the sticking observed are totally unacceptable. This formulation 11, obtained by direct tableting, is therefore the best compromise in achieving technical feasibility of the direct tableting form and satisfactory stability of the active principle.

The stability is also satisfactory via leaktight packaging of blister pack type, 45 μm aluminium, sealed by 20 μm aluminium (see Table 9 below).

TABLE 9

Stability, 24 months, Formulation 11
Conditions: 25° C., 60% Relative Humidity

| | 0 month | 1 month | 3 months | 6 months | 12 months | 24 months |
|---|---|---|---|---|---|---|
| Idazoxan hydrochloride content (mg/tablet) | 19.51 | 19.66 | 20.00 | 19.88 | 18.84 | 19.16 |
| Percentage of decomposition product 791011 | 0.24 | 0.66 | 0.74 | 1.06 | 1.19 | 1.64 |

Example 2

Examples of Formulations

Formulation 1:

| | |
|---|---|
| Idazoxan hydrochloride | 5% |
| Microcrystalline cellulose | 10% |
| Glyceryl behenate | 5% |
| Colloidal silica | 0.1% |
| Lactose monohydrate | q.s. for 100% |

This formulation makes it possible to manufacture tablets assaying between 10 mg and 30 mg of idazoxan hydrochloride packaged in all-aluminium blister packs.

Formulation 2:

| | |
|---|---|
| Idazoxan hydrochloride | 5% |
| Microcrystalline cellulose | 40% |
| Glyceryl behenate | 1% |
| Colloidal silica | 0.1% |
| Lactose monohydrate | q.s. for 100% |

This formulation makes it possible to manufacture tablets assaying between 10 mg and 30 mg of idazoxan hydrochloride packaged in all-aluminium blister packs.

Formulation 3:

| | |
|---|---|
| Idazoxan hydrochloride | 5% |
| Microcrystalline cellulose | 40% |
| Glyceryl behenate | 5% |
| Colloidal silica | 0.5% |
| Lactose monohydrate | q.s. for 100% |

This formulation makes it possible to manufacture tablets assaying between 10 mg and 30 mg of idazoxan hydrochloride packaged in all-aluminium blister packs.

Formulation 4:

| | |
|---|---|
| Idazoxan hydrochloride | 20% |
| Microcrystalline cellulose | 10% |

-continued

| | |
|---|---|
| Glyceryl behenate | 5% |
| Colloidal silica | 0.1% |
| Lactose monohydrate | q.s. for 100% |

This formulation makes it possible to manufacture tablets assaying between 10 mg and 30 mg of idazoxan hydrochloride packaged in all-aluminium blister packs.

Formulation 5:

| | |
|---|---|
| Idazoxan hydrochloride | 20% |
| Microcrystalline cellulose | 40% |
| Glyceryl behenate | 2% |
| Colloidal silica | 0.1% |
| Lactose monohydrate | q.s. for 100% |

This formulation makes it possible to manufacture tablets assaying between 10 mg and 30 mg of idazoxan hydrochloride packaged in all-aluminium blister packs.

Formulation 6:

| | |
|---|---|
| Idazoxan hydrochloride | 20% |
| Microcrystalline cellulose | 40% |
| Glyceryl behenate | 5% |
| Colloidal silica | 0.1% |
| Lactose monohydrate | q.s. for 100% |

This formulation makes it possible to manufacture tablets assaying between 10 mg and 30 mg of idazoxan hydrochloride packaged in all-aluminium blister packs.

Formulation 7:

| | |
|---|---|
| Idazoxan hydrochloride | 10% |
| Microcrystalline cellulose | 26.34% |
| Glyceryl behenate | 2% |
| Colloidal silica | 0.2% |
| Lactose monohydrate | q.s. for 100% |

This formulation makes it possible to manufacture tablets assaying between 10 mg and 30 mg of idazoxan hydrochloride packaged in all-aluminium blister packs.

N.B.: The results of the physicochemical analyses of these tablets given as examples (Formulations 1 to 7), manufactured on an industrial rotary press, after placing in a leaktight packaging, showed:
- a disintegration time for the tablets of less than 15 minutes immediately after manufacture and over time
- a percentage of dissolved active principle of greater than 80% in 30 minutes after manufacture and over time
- CV in content values of less than 6%
- a mean content of active principle in the tablets to ±5% of the theoretical dosage
- good stability over time, the sum of the impurities being less than 2% after 24 months at 25° C., 60% RH
- good microbiological quality after manufacture and over time Example 3

Stability and Decomposition Profile

A photostability study according to the ICH criteria showed no decomposition.

Furthermore, an accelerated and long-term conditions stability study was carried out, and the long-term stability of the polymorph of form I is shown in Table 10:

TABLE 10

| Batch of the form I | Long-term stability (in months) | | |
|---|---|---|---|
| | 25° C./60% RH[1] | 30° C./70% RH | 40° C./75% RH |
| OP2 | 24 | 24 | 9 |
| 500 | 24 | 24 | 6 |
| 501 | 24 | 24 | 6 |
| 503 | 9 | 6 | 6 |
| 504 | 9 | 6 | 6 |

[1]RH = relative humidity

Example 4

Analysis of the Solubility of the Polymorph of Form I

The solubility of the polymorph of form I in various solvents is shown in Table 11.

TABLE 11

| Batch of the form I | Water | Ethanol | Ethyl acetate |
|---|---|---|---|
| OP2 | Freely soluble | Soluble | Virtually insoluble |
| 500 | Freely soluble | Soluble | Virtually insoluble |
| 501 | Freely soluble | Soluble | Virtually insoluble |
| 503 | Freely soluble | Soluble | Virtually insoluble |
| 504 | Freely soluble | Soluble | Virtually insoluble |
| 507 | Freely soluble | Moderately soluble | Virtually insoluble |
| 508 | Freely soluble | Soluble | Virtually insoluble |

Example 5

Synthetic Processes 5.1. Processes for the Synthesis of Idazoxan Hydrochloride of the Prior Art Idazoxan hydrochloride can be synthesized according to the published method described below:

Preparation of 2-[2-(1,4-benzodioxanyl)]-2-imidazoline hydrochloride. A solution of sodium methoxide (1.45 g) in methanol (20 ml) is added in the space of one minute to a stirred solution of 2-cyano-1,4-benzodioxane (145 g) in methanol (870 ml) at ambient temperature. After stirring for a further 4 hours at ambient temperature, the solution is cooled and ethylenediamine (64.7 g) is added dropwise at a temperature of 5° C. A solution of hydrogen chloride in methanol (134 g of solution comprising 34.8 g of hydrogen chloride) is then added to the stirred solution in the space of 2 hours and at a temperature of 50° C. After a further 20 hours at 0-10° C., the precipitated ethylenediamine dihydrochloride is removed by filtration and the filtrate is reduced to 300 g under vacuum at 40° C. Ethylenediamine dihydrochloride is again removed and the remaining filtrate is subjected to evaporation under vacuum at 40° C. to complete dryness. The solid residue (225 g) is stirred with dichloromethane (1.1 liters) and dry hydrogen chloride is sparged in at 5-10° C. until a slight excess is obtained. The crude product is subsequently removed by filtration (172 g) and combined with a second crop (24 g) obtained by concentrating the filtrate under vacuum at 40° C. The crystallization of these two crops from ethanol with hot filtration and concentration of the filtrate under vacuum until 384 g are obtained gives an off-white crystalline product (175.5 g, 81%), melting point 207-208° C. If the ethylenediamine and the hydrogen chloride are added to the methanol in the reverse order, a similar yield is obtained.

5.2. Processes for the Synthesis of Idazoxan Hydrochloride with Polymorphs

Idazoxan hydrochloride comprising a polymorph of any one of the forms I can be synthesized according to the method described below:

(a) Stage 1. The first stage consists in obtaining 2-cyano-1,4-benzodioxane from the reaction of catechol and 2-chloroacrylonitrile in the presence of pulverized potassium carbonate and of a catalyst, tetrabutylammonium bromide, in a mixture of toluene and dioxane. The reaction is carried out at a temperature of between 80 and 90° C. After a double decoloration, the toluene is evaporated and an oily extract of 2-cyano-1,4-benzodioxane in the racemic form is obtained.

(b) Stage 2. In the presence of sodium methoxide, 2-cyano-1,4-benzodioxane gives an imidate, not isolated, which is further cyclized to idazoxan in the presence of ethylenediamine and of hydrochloric acid. The excess ethylenediamine is crystallized by addition of hydrochloric acid and then removed by filtration. Recrystallization of idazoxan hydrochloride is carried out from ethanol. The medicinal substance obtained corresponds to the racemic form I.

A stage of additional purification using different solvents makes it possible to obtain different polymorphs of idazoxan hydrochloride.

(c) Stage 3—Purification. Purification of the final compound is possible when any one of its characteristic features does not meet the specifications.

For the impurities such as sulphated ash, heavy metals and ethylenediamine content, the retreatment consists in returning to the base form, followed by liquid/liquid washing, before returning to the hydrochloride form. A recrystallization is then carried out.

In the case of nonconformity with respect to the clarity of the solution, the colouring of the solution, the pH of the solution, the 2-chloroacrylonitrile content and the associated substances (high-pressure liquid chromatography), the retreatment consists of a recrystallization.

In the case of nonconformity with respect to the water content and the residual solvents, drying is carried out.

This purification/recrystallization stage can be carried out using the following solvents: acetonitrile, n-propanol, methanol, ethanol, 1-butanol and n-butanol.

The form III is obtained by recrystallizing the form I with ethanol.

The form IV is obtained by recrystallizing the form I with 1-butanol.

An idazoxan hydrochloride monohydrate (form V) is obtained by reslurrying the form I in 5 volumes of an acetone/water mixture.

Example 6

Crystallographic Analysis by Powder X-Ray Diffraction on the Idazoxan Polymorphs I to V Crystallography by powder X-ray diffraction was carried out on the idazoxan forms I to V obtained in accordance with the process of the present invention as described in detail in Table 12 below.

TABLE 12

Samples of idazoxan polymorphs analysed by crystallography by powder X-ray diffraction

| Sample of polymorphs | Process |
|---|---|
| Form I | Examples 5.1 and 5.2 |
| Form II | Example 5.1 |
| Form III | Example 5.2 (ethanol) |
| Form IV | Example 5.2 (1-butanol) |
| Form V | Example 5.2 (water/acetone) |

The samples were analysed using a Philips PW 1730 device equipped with a horizontal goniometer CGR of type C and with a Cu anticathode ($\lambda=1.54051$ Å), operating at 40 kV and 20 mA.

The sample was prepared according to the standard operating procedure, in accordance with the instructions of the manufacturer, using a plate sample holder without spurious effects. The samples were analysed after gentle grinding using a pestle and mortar to guarantee good homogeneity.

It was observed that the melting and the decomposition of idazoxan hydrochloride do not make possible a thermal analysis study of the polymorphs within this temperature range. Only crystallography by X-ray diffraction can make possible the discovery of different crystalline forms.

FIG. 1 represents the X-ray diffraction diagram for the idazoxan polymorph of form I manufactured in accordance with the process of the present invention (Example 5.2); FIG. 2 represents the X-ray diffraction diagram for the idazoxan polymorph of form II manufactured according to the prior art (Example 5.1); FIGS. 3 and 4 represent the X-ray diffraction diagram for the idazoxan polymorphs of form III and IV respectively (Example 5.2); and FIG. 5 represents the X-ray diffraction diagram for the idazoxan polymorph of form V (Example 5.2). The data corresponding to the X-ray diffraction diagrams are presented in Tables 13 to 17 below:

TABLE 13

Idazoxan polymorph of form I

| Peak | Theta (degrees) | D (Å) |
|---|---|---|
| 1 | 4.0200 | 10.9872 |
| 2 | 6.6400 | 6.6613 |
| 3 | 6.9000 | 6.4115 |
| 4 | 7.0800 | 6.2493 |
| 5 | 8.0800 | 5.4801 |
| 6 | 9.0000 | 4.9238 |
| 7 | 9.9600 | 4.4534 |
| 8 | 10.8400 | 4.0956 |
| 9 | 11.7200 | 3.7919 |
| 10 | 12.1400 | 3.6626 |
| 11 | 12.3800 | 3.5927 |
| 12 | 12.9800 | 3.4293 |
| 13 | 13.300 | 3.3482 |
| 14 | 13.5200 | 3.2947 |
| 15 | 14.9000 | 2.9956 |
| 16 | 15.0600 | 2.9645 |
| 17 | 15.2400 | 2.9303 |
| 18 | 21.4000 | 2.1110 |

TABLE 14

Idazoxan polymorph of form II

| Peak | Theta (degrees) | D (Å) |
|---|---|---|
| 1 | 4.7400 | 9.3213 |
| 2 | 5.7200 | 7.7283 |
| 3 | 6.6800 | 6.6216 |
| 4 | 7.5000 | 5.9012 |
| 5 | 8.9200 | 4.9676 |
| 6 | 9.9600 | 4.4534 |
| 7 | 11.5200 | 3.8569 |
| 8 | 12.3000 | 3.6157 |
| 9 | 12.9400 | 3.4397 |
| 10 | 13.5400 | 3.2899 |
| 11 | 14.3000 | 3.1185 |
| 12 | 15.6800 | 2.8500 |
| 13 | 16.8600 | 2.6557 |
| 14 | 18.9000 | 2.3779 |

TABLE 15

Idazoxan polymorph of form III

| Peak | Theta (degrees) | D (Å) |
|---|---|---|
| 1 | 4.0400 | 10.9329 |
| 2 | 4.7000 | 9.4004 |
| 3 | 5.7400 | 7.7014 |
| 4 | 6.6200 | 6.6814 |
| 5 | 6.9200 | 6.3930 |
| 6 | 7.4600 | 5.9326 |
| 7 | 8.0400 | 5.5072 |
| 8 | 8.7800 | 5.0462 |
| 9 | 8.9800 | 4.9347 |
| 10 | 9.9800 | 4.4445 |
| 11 | 10.8200 | 4.1031 |
| 12 | 11.4600 | 3.8768 |
| 13 | 11.6400 | 3.8176 |
| 14 | 12.3200 | 3.6099 |
| 15 | 12.9400 | 3.4397 |
| 16 | 13.5400 | 3.2899 |
| 17 | 14.2400 | 3.1313 |
| 18 | 15.0600 | 2.9645 |
| 19 | 15.6200 | 2.8607 |
| 20 | 16.8400 | 2.6588 |

TABLE 16

Idazoxan polymorph of form IV

| Peak | Theta (degrees) | D (Å) |
|---|---|---|
| 1 | 4.8000 | 9.2050 |
| 2 | 5.9000 | 7.4933 |
| 3 | 6.8400 | 6.4675 |
| 4 | 7.3200 | 6.0454 |
| 5 | 8.0800 | 5.4801 |
| 6 | 8.6600 | 5.1156 |
| 7 | 9.4600 | 4.6864 |
| 8 | 9.6800 | 4.5809 |
| 9 | 11.1600 | 3.9796 |
| 10 | 11.4000 | 3.8969 |
| 11 | 11.9000 | 3.7354 |
| 12 | 12.2200 | 3.6390 |
| 13 | 12.6800 | 3.5090 |
| 14 | 13.8400 | 3.2200 |
| 15 | 14.4200 | 3.0930 |
| 16 | 14.9800 | 2.9799 |
| 17 | 18.1000 | 2.4793 |

TABLE 17

Idazoxan monohydrate of form V

| Peak | Theta (degrees) | D (Å) |
|---|---|---|
| 1 | 5.0400 | 8.7677 |
| 2 | 5.8400 | 7.5700 |
| 3 | 7.9400 | 5.5761 |
| 4 | 9.2800 | 4.7765 |
| 5 | 9.4400 | 4.6963 |
| 6 | 10.1200 | 4.3837 |
| 7 | 12.0200 | 3.6986 |
| 8 | 12.5600 | 3.5420 |
| 9 | 12.9200 | 3.4449 |
| 10 | 13.7400 | 3.2430 |
| 11 | 13.9400 | 3.1973 |
| 12 | 14.5200 | 3.0722 |
| 13 | 14.8200 | 3.0114 |
| 14 | 15.2800 | 2.9228 |
| 15 | 16.2800 | 2.7477 |
| 16 | 16.7400 | 2.6742 |

These results reflect the crystalline structure of the polymorphs.

The different degrees of crystallinity of the different forms examined have resulted in significant variation in the intensities, in particular with the substantially modified intensity of the X-rays at 4.02 degrees θ. The diffraction diagrams of the forms II, III and IV are visibly different from one another. For example, the diffraction diagram of the form II has three diffraction peaks at 5.52, 7.5 and 11.52 degrees θ. The peak at 4.04 degrees θ, characteristic of the form III, is not present in the diffraction diagram of the form II. The form III exhibits a diffraction peak at 4.70 degrees θ which is not present in the diffraction diagram of the form IV. The form IV exhibits two peaks at 8.78 and 8.98 degrees θ which are not present in the diffraction diagram of the form III. The diffraction diagram of the form V is also unique and easy to distinguish from the others.

Example 7

Differential Thermal Analysis on the Idazoxan Polymorphs I to V

Differential thermal analysis was carried out on the idazoxan polymorphs of form I to V obtained in accordance with the process of the present invention (Example 5.2).

The samples were placed in closed and crimped aluminium containers. Three samples of 4 mg of each of the forms I to V were analysed. The temperatures for the beginning of melting were determined in accordance with the instructions of the IUPAC by measuring the temperature at the intersection of the extended base line (linear portion of the differential thermal analysis curve) with the tangent of the steepest slope of the front side of the peak. The final temperatures correspond to the tip of the peaks. The equipment was calibrated using the enthalpy of fusion of indium (28.5 J/g) as reference value. The samples were subjected to two analyses at 10° C./min from 30 to 240° C. and from 150 to 240° C. The object of the second analysis was to determine with accuracy the temperatures of the beginning and end of melting. For this purpose, four determinations were carried out for each sample and the mean of these values, as well as the relative error, were calculated using the Student-Fischer tables (t=3.182 for P=0.05). The enthalpies were calculated in the same way but on the basis of five determinations (t=2.776, P=0.05).

A thermogravimetric analysis was carried out on 9.888 mg of idazoxan monohydrate of form V from 30 to 400° C., under nitrogen, at 10° C./min.

FIGS. 6 and 7 represent representative differential thermal analysis thermograms (as measured on the abovementioned device) for the forms I to V of idazoxan which are manufactured in accordance with the processes of the present invention.

No solid-solid transformation was observed in any sample during the increase in temperature before melting.

The results of the multiple samples are presented in Table 18:

TABLE 18

| | Differential thermal analysis | |
|---|---|---|
| Polymorph | Temperature of the beginning (° C.) | Temperature peaks (° C.) |
| Form I | 199.3 ± 0.3 | 207.5 ± 0.2 |
| Form II | 198.1 ± 0.5 | 203.9 ± 0.4 |
| Form III | 196.9 ± 0.3 | 203.8 ± 0.5 |
| Form IV | 200.4 ± 0.3 | 205.3 ± 0.5 |
| Form V | 201 ± 0.4 | 205.6 ± 0.4 |

As is shown by the data presented here, the forms I to V of idazoxan exhibit unique differential thermal analysis thermograms.

Idazoxan monohydrate of form V exhibits an endothermic peak, indicating the loss of a water molecule, at 87.5±0.4° C. with an enthalpy of dehydration of 207.6±5.6 J/g. A second endothermic peak begins at 201±0.4° C. and ends at 205.6±0.4° C., which corresponds to the melting point of the sample and occurs in the decomposition range of the molecule. This decomposition is displayed by an exothermic peak after melting situated in the vicinity of 220° C.

The endotherms of the different idazoxan polymorphs analysed can vary according to the speed of heating, that is to say the rate of the scanning, at which the differential thermal analysis is carried out, the calibration standards used, the calibration of the device, the relative humidity and the chemical purity. For any given sample, the endotherm observed can also differ from one device to another but it will generally remain within the ranges defined by the present document, provided that the devices are similarly calibrated.

Example 8

8.1. Racemization of Idazoxan in vitro

An asymmetry in the $C_2$ position of the idazoxan molecule gives rise to two enantiomers, the R(−) and S(+) forms. The lability of the proton in this position makes possible spontaneous interconversion between the two forms. Methods coming under physiological chemistry, biochemistry and biology were used to study the racemization of idazoxan in vitro.

The lability of the $C_2$ proton was studied by nuclear magnetic resonance spectroscopy so as to monitor proton-deuterium exchange in a physiological phosphate buffer (pH 7.4) at 37° C. Approximately 50% of the exchange had taken place after 80 minutes and the exchange was virtually complete after 4 hours.

Racemization of the two enantiomers in a phosphate buffer (pH 7.4) at 25 and 37° C. was studied by high-pressure liquid chromatography. The kinetics of racemization of the two enantiomers proved to be identical, with a racemization half-life of approximately 5 hours at 25° C. and 1 hour at 37° C.

The binding values of the $\alpha_2$-adrenoreceptors for the two enantiomers were evaluated using rat cortical tissue. In addition, the biological activity was evaluated by the inhibition of the hypothermia induced by guanabenz in mice. Initially, the S(+) form showed a binding affinity ten times greater than that of the R(−) form and proved to be 15 times more effective in the antagonism of the hypothermia. However, preincubation in a buffer at 37° C. for 1 h 30 for the binding test and for 4 hours in the behavioural model allowed it to be concluded that there was no perceptible difference in activity between the two enantiomers, which indicates that the equilibrium of the racemization had indeed been achieved.

8.2. Pharmacokinetics of the Enantiomers of Idazoxan

Young healthy male subjects were allocated at random to receive a single dose of each of the following substances on one occasion: 20 mg of idazoxan racemate (polymorph of form I); 10 mg of the R(−) enantiomer; 10 mg of the S(+) enantiomer. The pharmacokinetic parameters for each enantiomer are presented below in Tables 19 and 20.

TABLE 19

Pharmacokinetic parameters of R(−) idazoxan subsequent to a single administration of the racemate (20 mg) or of the enantiomer alone (10 mg)

| Component received | $C_{max}$ (ng/ml) | $T_{max}$ (hour) | $AUC_0$-∞ (ng · h/ml) | $t_{1/2}$ (hour) | $CL_{tot}/F$ (l/h) | $V_d/F$ (l) |
|---|---|---|---|---|---|---|
| Racemate | 11.9 ± 4.6 | 2.1 ± 0.7 | 58 ± 23 | 3.3 ± 0.4 | 170 ± 76 | 789 ± 315 |
| R(−) Idazoxan | 10.2 ± 3.9 | 2.5 ± 0.5 | 43 ± 19 | 3.1 ± 0.6 | 230 ± 92 | 988 ± 293 |
| S(−) Idazoxan | 1.3 ± 0.7 | 3.7 ± 0.5 | 11 ± 6 | 3.7 ± 0.4 | n.a. | n.a. | n.a.: Not applicable

TABLE 20

Pharmacokinetic parameters of S(+) idazoxan subsequent to a single administration of the racemate (20 mg) or of the enantiomer alone (10 mg)

| Component received | $C_{max}$ (ng/ml) | $T_{max}$ (hour) | $AUC_0$-∞ (ng · h/ml) | $t_{1/2}$ (hour) | $CL_{tot}/F$ (l/h) | $V_d/F$ (l) |
|---|---|---|---|---|---|---|
| Racemate | 8.3 ± 3.6 | 2.1 ± 0.7 | 44 ± 21 | 3.3 ± 0.4 | 245 ± 136 | 1137 ± 540 |
| R(−) Idazoxan | 1.6 ± 1.0 | 4.0 ± 0 | 14 ± 8 | 4.1 ± 0.5 | n.a. | n.a. |
| S(−) Idazoxan | 7.2 ± 5.1 | 2.1 ± 0.8 | 27 ± 13 | 7.8 ± 0.5 | 397 ± 205 | 1515 ± 692 | n.a.: Not applicable

The results indicate that the R(−) and S(+) forms of idazoxan exhibit different pharmacokinetic characteristics. The S(+) enantiomer exhibits an apparent clearance and a distribution which are approximately 1.5 times better than the R(−) enantiomer but a similar $t_{1/2}$, resulting in higher levels of R(−) in the plasma.

The two enantiomers are converted into one another according to a slow and limited process ($T_{max}$ of approximately 4 hours; $t_{1/2}$ for conversion of R(−) to S(+) of 5 hours and of S(+) to R(−) of 4 hours), the formation of R(−) being slightly greater than that of S(+). The pharmacokinetic characteristics of each enantiomer, after administration of the racemate, combine the pharmacokinetic characteristics of the enantiomer which are determined after administration of the enantiomer in isolation, suggesting that no interaction takes place between the enantiomers when they are administered together. The concentrations of S(+) and R(−) peak and decline at a similar rate and R(−) circulates in a greater proportion than S(+). The three medicaments administered were all well tolerated.

Example 9

Use of Idazoxan as Medicament for the Treatment of Schizophrenia

Idazoxan has formed the subject of a double-blind study with a placebo as control on 17 patients suffering from schizophrenia or from schizoaffective disorders regarded as resistant to treatment with conventional neuroleptics (R. E. Litman, W. W. Hong et al., J. Clin. Psychopharmacol., August, 13(4), 264-7 (1993); R. E. Litman, T. P. Su et al., Br. J. Psychiatry, May, 168(5), 571-9 (1996)).

The treatments of the patients were modified so as to stabilize them for at least 2 weeks with fluphenazine hydrochloride, benzotropine mesylate being used to control the extrapyramidal symptoms (one of the patients was stabilized with thioridazine because of serious extrapyramidal symptoms). Idazoxan was added at the initial dose of 20 mg twice daily and the dose was gradually increased by 20 mg on each occasion over two weeks up to an optimum steady dose, with a target dose of 120 mg/day, maintained for at least 4 weeks. The dosage of the idazoxan was gradually reduced by 20 mg per day over 2 weeks, while the patients were administered with fluphenazine alone for at least 3 weeks. After a period of therapeutic withdrawal, 12 of the patients received clozapine, at an optimum dosage, for at least 5 weeks.

The addition of idazoxan to the treatment with fluphenazine led to a significant reduction in the symptoms in comparison with a fluphenazine monotherapy. Improvements were observed with the Bunney-Hamburg global psychotic assessment scale, the total score of the abbreviated psychiatric assessment scale, the negative symptoms of the abbreviated psychiatric assessment scale and the positive symptoms of the abbreviated psychiatric assessment scale, including as regards unusual thoughts and paranoic suspicion. Even though the improvement has proved to be modest (a reduction of the order of 10 to 15% in the total score of the abbreviated psychiatric assessment scale), it has proved to be of a comparable level to that obtained in the case of recourse to other non-neuroleptic medicaments for enhancing the effect of neuroleptic agents. The improvements in the total score and in the positive symptoms of the abbreviated psychiatric assessment scale correlate with the modifications observed in the plasma and urinary noradrenergic indicators. In addition, the treatment with idazoxan in combination with fluphenazine has proved to withstand comparison with that with clozapine alone.

What is claimed is:

1. A polymorphic form III of idazoxan wherein the X-Ray spectra comprises characteristic peaks at 4.0400, 4.7000, 5.7400, 6.6200, 6.9200, 7.4600, 8.0400, 8.7800, 8.9800, 9.9800, 10.8200, 11.4600, 11.6400, 12.3200, 12.9400, 13.5400, 14.2400, 15.0600, 15.6200 and 16.8400 degrees θ; and the differential thermal analysis thermogram exhibits a single maximum value at approximately 203.8±0.5.

* * * * *